United States Patent [19]

Ghebre-Sellassie et al.

[11] Patent Number: 4,600,645
[45] Date of Patent: Jul. 15, 1986

[54] PROCESS FOR TREATING DOSAGE FORMS

[75] Inventors: Isaac Ghebre-Sellassie, Randolph; Robert H. Gordon, Dover; Michael R. Harris, Budd Lake; Russell U. Nesbitt, Jr., Somerville, all of N.J.

[73] Assignee: Warner-Lambert Company, Morris Plains, N.J.

[21] Appl. No.: 696,955

[22] Filed: Jan. 31, 1985

[51] Int. Cl.⁴ .................. A61K 9/00; A61K 15/00; A61K 21/00
[52] U.S. Cl. .................... 428/403; 424/19; 424/21; 427/3; 428/407
[58] Field of Search ............. 427/3; 424/19, 21; 428/403, 407

[56] References Cited

U.S. PATENT DOCUMENTS

| | | | |
|---|---|---|---|
| 3,173,839 | 3/1965 | Nicholson | 427/3 |
| 3,909,444 | 9/1975 | Anderson et al. | 427/3 X |
| 3,935,326 | 1/1976 | Groppenbacher | 427/3 |
| 4,248,856 | 2/1981 | Guley et al. | 424/19 X |
| 4,258,179 | 3/1981 | Kawata et al. | 427/3 X |
| 4,287,221 | 9/1981 | Tonedachi et al. | 427/3 |
| 4,289,795 | 9/1981 | Bogentoft et al. | 427/3 |
| 4,302,440 | 11/1981 | John et al. | 427/3 X |
| 4,330,338 | 5/1982 | Banker | 424/35 X |
| 4,385,078 | 5/1983 | Onda et al. | 427/3 |

FOREIGN PATENT DOCUMENTS 2057876 4/1981 United Kingdom .
2087235 5/1982 United Kingdom .

Primary Examiner—James R. Hoffman
Attorney, Agent, or Firm—Sandra M. Person

[57] ABSTRACT

The problems of tackiness and long curing times usually associated with the treatment of dosage forms are overcome via the use of a new curing process. That process involves: (1) coating a drug with a sustained release formulation, (2) immediately coating with a water-soluble overcoat, (3) drying, and (4) recovering the coated dosage form.

8 Claims, 1 Drawing Figure

Release profiles of pellets that were cured at
□ 58° for one hour using the new procedure and
○ 60° for one week in an oven.

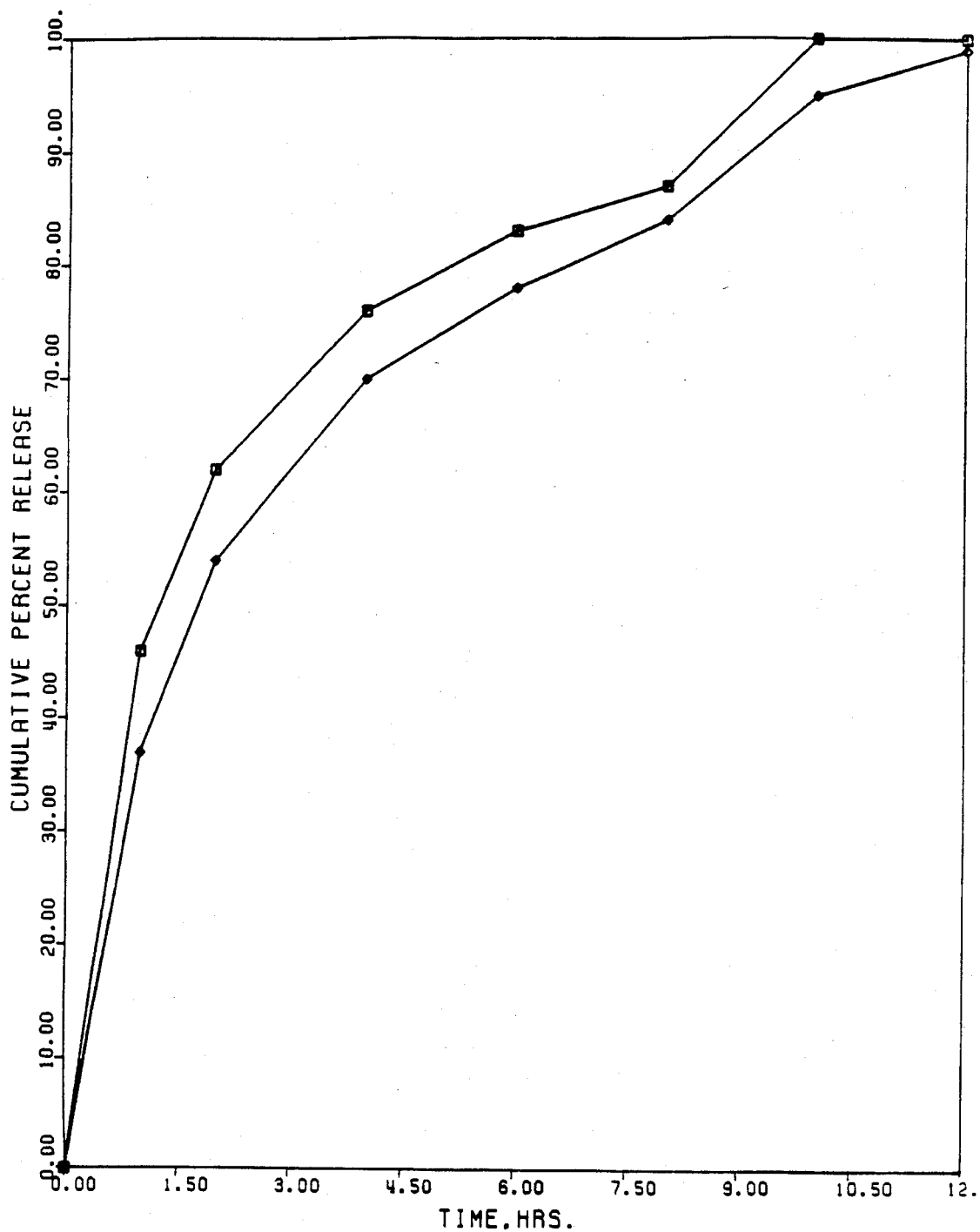
Release profiles of pellets that were cured at
▫ 58° for one hour using the new procedure and
◊ 60° for one week in an oven.

PROCESS FOR TREATING DOSAGE FORMS

BACKGROUND

Recently, due to stringent government regulations and the safety hazards associated with the use of organic solvents in coating systems for dosage forms, emphasis has shifted from solvent-based to water-based coating formulations. New polymeric dispersions have been developed and intensive research is being conducted to maximize the use of water dispersible colloidal particles. However, these aqueous formulations have generally exhibited shortcomings during the coating process.

One major problem is the tackiness which occurs during the curing of polymeric coatings. Although elevated temperatures are required to drive off water rapidly and deposit a film on the product, usually moderate temperatures (30°-50°) are employed in order to avoid the tackiness that has been frequently observed. Once the product is coated, the deposited film requires treatment at lower temperatures for extended periods of time to fully coalesce the polymer beads and ensure a continuous film. If elevated temperatures are employed, coalescence time may be shortened and reproducible release profiles achieved. However, the film usually becomes tacky and makes product handling difficult.

THE INVENTION

This invention deals with a process that substantially eliminates the tackiness problem and significantly reduces the curing time for coatings from days down to minutes or hours. In accordance with the invention, the product is first coated under suitable conditions using the appropriate formulation, followed immediately by a water-soluble overcoat. Spraying is then terminated and the product temperature is elevated to the desired level. The process is continued until complete coalescence of the film is attained.

The optimum temperature and time to be used will depend upon the type of formulation, coating level and the type of polymeric dispersion. The overcoat is composed of a single agent or a combination containing one or more water-soluble, natural or synthetic polymers such as cellulosic derivatives, and polyethylene glycols. Pharmaceutical additives, such as talc or kaolin, may be added to the overcoat formulation to help reduce tackiness while the overcoat is applied.

In one preferred embodiment, drug pellets are coated with a sustained-release composition which contains ethylcellulose, triethyl citrate, kaolin, and water. The coated pellets are then heated to temperatures on the order of about 30° C. to about 70° C. for periods of about 15 minutes to about 3 hours.

An overcoat formulation containing hydroxypropyl methylcellulose, polyethylene glycol, talc, and water is then applied to the pellets. The over-coated pellets do not exhibit the tackiness generally associated with coated dosage forms. The overcoat dries in 5 to 10 minutes.

OBJECTS OF THE INVENTION

It is one object of the invention to provide a process for treating pharmaceutical dosage forms.

ADVANTAGES OF THE INVENTION

The process described herein has several advantages over known processes of treating dosage forms. In addition to solving several handling problems—i.e., alleviating tackiness and slow curing—the process of the invention produces treated dosage forms whose release profiles are superior to those produced in accordance with known procedures.

Time and energy requirements are also lessened when using the subject invention. The coating process can be carried out using only one coating device, resulting in considerable savings.

Other objects and advantages will become apparent from a consideration of the following description.

DESCRIPTION OF THE INVENTION

The process of treating dosage forms in accordance with the invention involves:

(1) coating a drug-containing substrate with a sustained release formulation; and (2) coating the product of step (1) with a water-soluble overcoat; and (3) recovering the treated dosage form.

THE SUBSTRATE

Substrates which can be coated in accordance with the inventive process encompass a wide variety of materials. While it is preferred that they contained one or more drugs as the principle active ingredients, other ingestible substances, e.g. vitamins, minerals, nutrients and the like, can be substituted for all or part of the drugs(s) in the substrate.

Useful drugs include antihistamines, antihypertensives, tranquilizers, etc. One preferred group of drugs to be treated includes antihistamines, such as diphenhydramine and pharmaceutically acceptable derivatives/precursors thereof. Diphenhydramine and diphenhydramine hydrochloride are highly preferred ingredients for inclusion in the drug-containing substrate. Other drugs whose taste or other characteristics dictate a need for delayed/sustained release, e.g., cholestyramine and procainamide and its salts, are operable.

The drug-containing substrate can also include one or more of a wide variety of additives conventionally employed in solid dosage forms, e.g. carriers, flavor enhancers, colorants, and the like. When such additives are employed, they are present in such quantities that the quantity of active ingredient—e.g. drugs—which is present in the substrate is from about 5.0 to about 95.0 wt %, based on the total weight of the drug-containing substrate.

While the use of solid materials in the drug-containing substrate is preferred, the use of liquid ingredients, with or without suitable solid absorbents therefor, is also contemplated. The process of the invention is, with minor adjustment, suitable for treating liquid substrates.

THE SUSTAINED RELEASE FORMULATION

The first coating applied to the drug containing substrate is particularly formulated so that, after the dosage form is ingested, the drug or other active ingredient contained in the substrate is taken up by the body in a slow and sustained fashion. That is, the dosage release curves which result from the use of the initial coating are smooth, almost linear, curves when cumulative percent release is plotted against time.

Suitable formulations for use in the initial coatings contain water soluble and/or water dispersible matrices to which suitable ingredients have been added in order to reduce the tackiness and curing time of the coated substrate.

Typical matrices are polymeric materials such as cellulosic ethers. Aquacoat®, made by FMC, is an example of a highly preferred polymeric dispersion matrix. It is composed of ethylcellulose colloidal particles dispersed in water with cetyl alcohol and sodium lauryl sulfate added as stabilizers. Mixtures of matrices are operable.

Useful additives in the first coating include inert solids, e.g. clays and ion exchange materials which modify the release of the active ingredient from the substrate through the coating. Talc and kaolin are preferred.

Other additives, e.g. hydrophilic polymers such as polyethylene glycols can be employed. Triethyl citrate, a plasticizer, is a preferred processing aid. Mixtures of such additives are contemplated.

The relative quantities of the matrix material in the sustained release coating will be on the order of about 50.0 to about 80.0 wt %, based in total coating solids weight. Other additives, if present, will combine about 50.0 to about 20.0 wt %, based on total solids.

Since the coating is to be applied from an aqueous vehicle, solvents and other non-aqueous ingredients need not be used. The quantity of water present during the first coating operation depends upon such factors as the nature of the substrate and the type of equipment employed for the coating operation.

THE HYDROPHILIC OVERCOAT

The second coating composition, or overcoat, is designed to enhance the processability of the final product. It is the overcoat which significantly reduces the outlay in time and energy generally associated with treating the coated dosage forms.

The overcoat or second coating of the invention, like the first or base coat, is applied from an aqueous vehicle. The matrix of this second coating contains one or more hydrophilic, preferably highly water-soluble materials of monomeric or polymeric nature. One preferred matrix is hydroxypropylmethyl cellulose. Other suitable matrices include hydroxypropyl cellulose and the like. Mixtures are operable.

The use of hydrophilic matrices is preferred. However, non-hydrophilic matrices may be used in combination with suitable amounts of fillers to yield properties similar to those attained using hydrophilic matrices. For instance, a water-insoluble hydrophilic polymer, e.g., an ethyl cellulose polymer containing major amounts—i.e., 30–90% of talc, kaolin or other filler, will give similar results as a hydrophilic overcoat.

To assist in the flow properties of this coating when applied and in the subsequent handling of the overcoated dosage form, conventional processing aids, e.g., surfactants, fillers, etc. can be employed. One preferred group of surfactants are silicon polymers.

Polyethylene glycols and other well-known hydrophobic polymers are highly preferred as additives. Polyethylene glycol 3350 is particularly preferred when aqueous hydroxypropylmethy cellulose is the matrix.

Any of the optional ingredients employable in the base coating, described above, can be employed in the overcoat formulation. The amount of matrix material in the overcoat composition will range from about 0.01 to about 100% wt % based on total solids weight.

COATING PROCEDURES

The two-step coating process carried out in accordance herewith can be effected using conventional coating equipment. Suitable devices for applying the initial, or base, coating include fluidized bed granulation and drying devices and the like. The one preferred device is the Rotor Granulator made by Glatt.

In order to save time in the overall process, it is preferred that, following the initial coating step, the base-coated substrate be allowed to sit, with optional heat treatment to temperatures of about 45° C. to about 70° C., and preferably about 55° C. to about 60° C., to coalesce the matrix particles, so that a useful film results. When heat is employed it is generally used for about 15 to about 60 minutes, preferably about 20 to about 40 minutes.

The application of the second, or overcoat, formulation can be carried out using the same equipment as was used for the base coat. One preferred embodiment requires the use of only one type of device with continuous coating steps.

The drying temperatures and times to be used on the overcoat will be about 30 to about 80° C., for about 2 to about 15 minutes. Generally, preferred temperatures and times are about 45 to about 60° C. and about 5 to about 10 minutes, respectively. The drying parameters used in treating the based coated intermediate—i.e., the product of step (1)—will be operable in this step as well.

Recovery of the final dosage form is carried out using conventional techniques. Once the overcoat has dried, the treated dosage forms are processed via well-known operations, such as are generally employed to accommodate packaging and/or storage requirements.

Other conventional techniques for handling oral dosage forms can be employed before, during and/or after the two-step process outlined above.

The chemical and physical nature of the substrate will dictate the final form which the preparations of this invention will take. For example, diphenydramine hydrochloride is a bitter-tasting solid substance. Since it is an antihistamine, it is an excellent candidate for applicants' process.

While ingestible pellets are a preferred final product, other coated dosage forms, e.g. powders, capsules and the like, are also contemplated.

The following examples demonstrate the effectiveness of the invention.

EXAMPLE I

The coating formulations used in this example were:

| (a) Sustained-release (base) formulation | |
|---|---|
| 1. Aquacoat ® | 465 gm |
| 2. Triethylcitrate | 186 gm |
| 3. Kaolin | 51 gm |
| 4. Purified water | 990 gm |
| (b) Overcoat formulation | |
| 5. Hydroxypropylmethylcellulose | 6.0 gm |
| 6. Polyethylene Glycol 3350 | 1.2 gm |
| 7. Talc | 1.0 gm |
| 8. Purified water | 91.8 gm |

I. Sustained Release Coating: (Parameters for 5 kg of pellets)
  Use 0.564 kg of coating dispersion for 1 kg of pellets.
  A. Disperse 3 in 4 and hydrate for 10 minutes.

B. Add A and 2 to 1 (in that order) and mix for 10 minutes after each addition.

C. Place the drug pellets into Glatt Rotor-Granulator container (5 kg in Glatt Model GPCG-5).

D. Coat C with B using 1.2 mm nozzle orifice, atomizing pressure set at 2.5 bars, flap opening=40%, air inlet temperature=45° C. and bed temperature=32°-85° C., rotor=250 rpm. Spray 8.0% of coating suspension at the rate of 4.0 ml/minute per 1 kg pellets. Spray remainder of the coating suspension at the rate of 10.0 ml/minute per 1 kg pellets.

II. Aqueous Overcoat:

Use 0.415 kg of coating dispersion for 1 kg of core pellets.

E. Add 6 to about 90% of 8, heat to 60° C. and sprinkle in 5. Cool to room temperature with mixing. Continue mixing until dissolved. Disperse 7; continue mixing throughout the coating process.

F. Coat pellets from I in Rotor-Granulator with E immediately after the sustained release coating using a 1.2 mm nozzle orifice, atomizing pressure set at 2.5 bars, air inlet temperature=65° C. and bed temperature=45°-50° C. Spray at the rate of 24 ml/minute per 1 kg of pellets. Dry the coated pellets for 30 minutes at an inlet air temperature of 70° C. and rotor speed of 100 rpm.

BRIEF DESCRIPTION OF THE DRAWING

The FIGURE depicts the release profiles of diphenhydramine pellets, a portion of which were cured at 60° for one hour only using the claimed procedure (lower curve) and another portion which were further stored at 60° for one more week in an oven (upper curve). The similarity of the curves underscores the efficiency of applicants' curing process.

Reasonable variations, such as those which would occur to a skilled artisan, can be made herein without departing from the scope of the invention.

We claim:

1. A curing process for coated pharmaceutical dosage forms comprising the steps of:
   (1) coating a drug-containing substrate with a sustained release formulation,
   (2) immediately coating the product of step (1) with a water-soluble overcoat,
   (3) drying the product of step (2) for about 15 to about 60 minutes, and
   (4) recovering the coated dosage form.

2. The process of claim 1 wherein the formulation employed in step (1) contains a water-dispersible polymer, a filler and a plasticizer.

3. The process of claim 2 wherein the overcoat contains a water-soluble polymer.

4. The process of claim 3 wherein the drug-containing substrate is a pellet.

5. The process of claim 4 wherein steps (1) and (2) are carried out in the same device without removal of the product of step (1) prior to step (2).

6. The dosage form produced by the process of claim 3.

7. The dosage form produced by the process of claim 2.

8. The dosage form produced by the process of claim 4.

* * * * *